United States Patent [19]

Pinchuk

[11] Patent Number: 4,769,030
[45] Date of Patent: Sep. 6, 1988

[54] MONOMER AND USE THEREOF IN CRACK PREVENTION OF IMPLANTED PROSTHESES

[75] Inventor: Leonard Pinchuk, Miami, Fla.

[73] Assignee: Corvita Corporation, Miami, Fla.

[21] Appl. No.: 43,540

[22] Filed: Apr. 28, 1987

[51] Int. Cl.$^4$ .......................... A61F 2/06; A61F 2/02; A01N 1/02
[52] U.S. Cl. ............................................. 623/1; 623/2; 623/3; 623/11; 427/2; 427/412.1; 427/412.3
[58] Field of Search ...................... 427/2, 412.1, 412.3; 623/6, 11, 12, 14, 2, 3, 1

[56] References Cited

U.S. PATENT DOCUMENTS 4,652,459  3/1987  Engelhardt ............................ 427/2

OTHER PUBLICATIONS

Cranley, "Isocyantoethyl Methacrylate: A Latent Crosslinker for Coating and Adhesive Resins", The Dow Chemical Co., 1983.

Primary Examiner—Michael R. Lusignan
Attorney, Agent, or Firm—Lockwood, Alex, Fitzgibbon & Cummings

[57] ABSTRACT

Monomers are provided which are reaction products between an aromatic isocyanate and an acrylate having a terminal active hydrogen moiety. The monomers are especially easy to synthesize and have an extremely low vapor pressure at room temperature such that they are substantially non-volatile at room temperature. The monomers are also readily reacted at room temperature without the need of catalysts. The monomers are especially suitable for use as primers in connection with the application of crack preventative compositions to medical devices that are intended for in vivo implantation.

16 Claims, No Drawings

MONOMER AND USE THEREOF IN CRACK PREVENTION OF IMPLANTED PROSTHESES

BACKGROUND AND DESCRIPTION OF THE INVENTION

The present invention generally relates to a particular group of monomers and to their use in crack prevention of implanted prostheses. More particularly, the monomers include an active terminal isocyanate group and an active terminal acrylate group, such monomers being reaction products of an aromatic diisocyanate and an acrylate or a methacrylate. These monomers have exceptionally low vapor pressures at room temperature and exhibit a variety of uses including its particular usefulness as a coupling agent or primer coating for applying a crack-preventative composition such as a silicone rubber material to an implantable polymeric surface of a medical prosthesis, the polymeric surface being one that will crack when subjected to implantation for substantial time periods if it is not thus treated.

Reactive monomers or molecules that are easy to handle are generally sought after for a variety of reasons and uses. For example, a reactive monomer that possesses numerous advantageous properties with respect to its reactability is 2-isocyanate ethyl methacrylate, also referred to as isocyanatoethyl methacrylate (IEM), which is available from The Dow Chemical Company as a latent crosslinker for coating and adhesive resins. Such is a difunctional monomer with an aliphatic isocyanate functionality and a vinyl polymerizable double bond. Either end of this molecule can be reacted first, leaving the other functionality for latent reaction, the isocyanate group reacting, for example, with active hydrogen compounds, and the methacrylate functionality, for example, allowing copolymerization with vinyl monomers. Applications for IEM generally fall into three categories: polyisocyanates made by polymerizing the methacrylate group, vinyl functionalized resins made by reacting the isocyanate group with polyfunctional molecules, and polymerizable derivatives made by reacting the isocyanate group with monofunctional reagents. In addition to being useful as a latent crosslinker, IEM is suitable for use as a graft site for making resins suitable for coatings or adhesives.

Although a monomer such as IEM has many outstanding properties and exhibits exceptional versatility and suitability for numerous applications, a monomer such as IEM does have an especially troublesome disadvantage. The 2-isocyanate ethylmethacrylate monomer is extremely difficult to handle due to its high vapor pressure at room temperature, and the monomer is limited to use within fume hoods or glove boxes. Moreover, although such an IEM type of monomer possesses the desired reactive properties referred to hereinabove, the aliphatic nature of the carbon atoms that are alpha to the isocyanate tends to retard the reactivity of the isocyanate, thereby typically requiring a catalyst in order to react the isocyanate. Catalysts that are needed in this regard often poison other catalysts such as platinum that might be required for a particular reaction sequence. Also, the catalysts needed for IEM often preclude co-reactions of free radical polymerized polymers such as silicone rubbers.

Accordingly, there is a need for a monomer or molecule that possesses many of the properties of a molecule such as IEM, but which does not bring with it the extremely difficult handling problems that are associated with a high vapor pressure monomer such as IEM. Furthermore, additional advantageous attributes could be realized if such a monomer exhibited an isocyanate reactivity that is greater than that of a monomer such as IEM and that does not require a catalyst in order to react the isocyanate. Additionally, a monomer such as IEM can be expensive and difficult to synthesize because an isocyanate group has to be formed at its terminal location without disturbing other reactive groups on the reactant molecule.

By the present invention, a monomer is provided which has reactivity properties along the lines of those of a monomer such as IEM, but it has an extremely low vapor pressure, which permits its use in ambient air environments. The monomer includes a terminal isocyanate site and a terminal acrylate or methacrylate site, and it is a reaction product of an aromatic diisocyanate and an acrylate or methacrylate having a reactive hydroxyl group, amide group or the like that reacts with one of the isocyanate groups of the aromatic diisocyanate in order to form the monomer according to this invention. The reaction proceeds readily and inexpensively on a generally equimolar basis. Included in the useful applications of the monomer is its use as a coupling agent or primer, particularly its advantageous properties that enable it to enhance the application of a crack preventative component to a prosthesis having a biocompatible polymeric surface in order to thereby substantially prevent surface fissuring, cracking or crazing which would otherwise be exhibited by the biocompatible polymer under in vivo conditions.

It is accordingly a general object of the present invention to provide an improved monomer having a reactive vinyl moiety and an extremely reactive isocyanate moiety.

Another object of this invention is to provide an improved monomer that is suitable for use as a coupling agent and that exhibits an extremely low vapor pressure at room temperature so that it may used in ambient air environments.

Another object of this invention is to provide an improved method for treating a polymeric material to substantially prevent surface fissuring, cracking or crazing of the polymer under in vivo conditions, which treatment method includes the use of a coupling agent.

Another object of the present invention is to provide an improved method for forming an implantable device which utilizes an advantageous coupling agent having a low vapor pressure.

Another object of the present invention is to provide an improved implantable device that incorporates a coupling agent having a low vapor pressure to pretreat the device for applying a crack preventative component thereto.

These and other objects, features and advantages of this invention will be clearly understood through a consideration of the following detailed description.

DESCRIPTION OF THE PARTICULAR EMBODIMENTS

Monomers according to this invention include a terminal isocyanate group and a terminal acrylate, preferably a methacrylate, group. The monomer has the following structure:

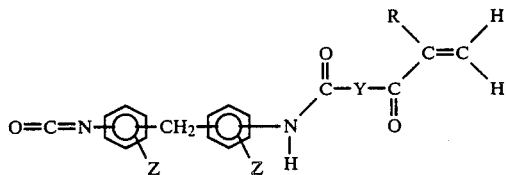

wherein R is H or CH₃ and Y is NH or X—R₁—X, wherein X is O or NH and R₁ is a hydrocarbon chain of from about 1 to about 6 carbon atoms. Z is H or a hydrocarbon chain of from about 1 to about 3 carbon atoms.

Generally speaking, the methacrylate structure (when R is CH₃) is preferred in order to enhance the hydrolytic stability of the monomer. It is further preferred that Z is H and that Y is X—R₁—X, with both X atoms being oxygen, and with R₁ having 1, 2 or 3 carbon atoms, most preferably 2 carbon atoms. Accordingly, the most preferred monomer is 2-(methylene bisphenyl isocyanate) ethyl methacrylate.

In forming the monomer from the aromatic diisocyanate and the acrylate or methacrylate, the two components are readily reacted, preferably in a solvent system, the reaction typically being exothermic. During the reaction, one of the isocyanate groups from the aromatic diisocyanate reacts with a reactive terminal group which is typically on the end of the acrylate molecule which is generally opposite to the acrylate or methacrylate group, such reactive group usually being a hydroxyl group, an amino group, or any other group with an active hydrogen atom. The preferred diisocyanate reactant is methylene bisphenyl isocyanate, including the isomeric forms thereof such as 1,4-methylene bisphenyl isocyanate and 1,3-methylene bisphenyl isocyanate. The positioning may be ortho, meta or para, which is also the case for the location of the Z ring substituent, when present.

The acrylate reactants for synthesizing the monomers include 2-hydroxyethyl methacrylate, 2-hydroxyethyl acrylate, acrylamide, hydroxymethyl methacrylate, hydroxymethyl acrylate, 2-aminoethyl methacrylate, and the like. Especially preferred is 2-hydroxyethyl methacrylate.

The product of these reactants, which is illustrated by the previously specified formula, has aromatic groups generally alpha to the terminal isocyanate group and a corresponding extremely low vapor pressure at room temperature which is typically lower than the vapor pressure at room temperature of the aromatic isocyanate reactants such as methylene bisphenyl isocyanate. Prior art molecules which are not products of these reactants, such as 2-isocyanate ethyl methacrylate, are extremely difficult to handle due to their high vapor pressures at room temperature. Rather than exhibiting aromatic groups alpha to the isocyanate group, which is the case for the present monomers, these prior art molecules exhibit an aliphatic structure alpha to the isocyanate, which does not impart the same degree of reactivity to the isocyanate, often requiring a catalyst in order to react the isocyanate.

The difunctional monomers according to the present invention have properties that render same suitable for a wide variety of uses. They can be used as adhesives in ambient air environments. The aromatic nature of the isocyanate group allows for the use of the monomers at room temperature and without the need of catalysts. The terminal isocyanate portion of the monomers can react with nucleophiles such as amines, hydroxyl groups, sulfur groups and the like. The terminal acrylic moiety, or double bond group, can be used as a site for free radical attachment to residual double bonds on polymers such as silicone rubbers, hydrogels, methylmethacrylates such as plexiglass, tetrafluoroethylene fluorocarbon polymers and the like, or on these same polymers during insert molding or synthesis operations.

When the monomers according to this invention are bonded to a substrate, the bond is covalent in nature, typically by virtue of an allophanate type of bonding, rather than being an interpenetrating type of bonding, in order to provide especially advantageous hydrolytic stability and strength when compared with other adhesives.

More particularly, the monomers can be used to adhere free radical initiated polymers such as silicones, hydrogels, polycarbonates, methacrylates and the like to substrates such as metals, polyurethanes, polyamides, methacrylates, hydrogels, and any other polymers that are reactive to isocyanates. The monomers can also be incorporated into a polyurethane prepolymer resin to adhere free radical polymers to polyurethanes or polycarbonates, or other polar solvent soluble molecules. Other uses of these monomers include graft polymer intermediates for the bonding of drugs to medical devices, or for the bonding of tetrafluoroethylene fluorocarbon polymers or silicone materials to medical devices in order to form coatings thereon to decrease the surface tension of the devices. The monomers are also useful in connection with the bonding of drugs to silicone substrates and to vascular grafts having surfaces of biocompatible polymers.

Especially important is the ability of the monomers to function as primers or coupling agents for applying a crack preventative composition onto a biocompatible polymeric surface of a medical device or implantable prosthesis. Exemplary advantageous crack preventative compositions in this regard include those of the silicone rubber type, which compositions typically include a silicone rubber type of material and a solvent therefor. Catalysts and/or crosslinkers or other systems for curing the silicone rubber type of material may be included. The monomers according to this invention are especially suitable for use as a coupling agent, bonding agent or primer coating in order to enhance the adherence to and adsorption onto the biocompatible polymeric surface of the crack preventative composition.

The monomers are especially suitable for promoting adherence to urethane polymers and polymers of similar properties. It is believed that the monomers link onto a urethane type of surface by way of forming allophanate types of structures and that the double bonds of the monomers generally covalently bond to the surface of the urethane type of material at the nitrogen atom of an isocyanate group of the urethane type of material.

Exemplary biocompatible polymeric materials with which the monomers can be used include various polyurethanes, including copolymers thereof such as poly(fluorosilicone urethane) copolymers, polyolefins such as a polypropylene, and acrylate polymers such as polymethylmethacrylate. Materials of this type are significantly enhanced with respect to resistance to cracking after in vivo implantation when they are treated with a crack preventative composition after having been first treated with monomers in accordance with this invention which, in such instance, perform as primer coatings to enhance the adherence of the crack preventative composition onto the biocompatible polymer. When desired, for example in conjunction with the manufacture of vascular grafts spun from such polymeric fibers, the polymeric fibers may be subjected to annealing conditions prior to treatment with the crack preventative composition. Also, the adsorption of the crack preventative composition onto the biocompatible polymer is assisted if the components are chosen such that the biocompatible polymeric material has a surface tension which is greater than that of the crack preventative material.

Generally speaking, the use of the monomers in primer coat compositions can be more advantageously utilized in those instances where the implantable device or the like has a relatively large and smooth surface area, such as would be the case for a cardiac pacer lead insulator or an artificial heart diaphragm, which structures present a unitary surface area that is generally smooth and without any significant undulations or porosity. Other similar types of products include artificial heart valve leaflets and sewing cuffs and the like. Other implantable medical devices which can benefit from the use of the monomers in primer coat compositions in advance of the application of a crack preventative composition include vascular grafts that are spun from extruded fibers on an apparatus including an elongated mandrel and a spinnerette assembly that rotate with respect to each other while the spinnerette traverses a pathway generally along the elongated mandrel. Other such products include permanent sutures and loops or haptics of intraocular lens implants.

The monomers may be incorporated into coupling agent compositions or primer coating compositions in which the monomer is dissolved or dispersed in association with solvents such as dimethylacetamide, dimethylformamide, isopropanol, acetone, water and the like. Usually, the most efficient utilization of solvents is realized when the solvent of the coupling agent composition or primer coating composition incorporates the solvent within which the monomer had been formed during the reaction between the aromatic isocyanate reactant and the acrylate reactant, for example solvents such as dimethylacetamide and dimethylformamide.

Crack preventative compositions that can be advantageously applied to biocompatible polymeric surfaces with a primer composition including the monomers as discussed herein are crack preventative compositions that include a crack preventative agent that is a silicone rubber type of component. A preferred component in this regard is a siloxane having groups which can be generally represented by the formula —O—Si—O—. A representative siloxane component, prior to curing, can be presented by the formula:

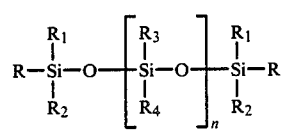

wherein each of R, $R_1$, and/or $R_2$ can be a group such an ester moiety, an acetoxy moiety, an alcohol moiety and the like that are involved in crosslinking, curing or polymerizing of the siloxane. $R_3$ and $R_4$, as well as $R_1$ and $R_2$, can each be aliphatic or aromatic groups such as methyl, ethyl, propyl, phenyl, or substituted aliphatics or aromatics containing halogen moieties or other groups, for example 3,3,3-trifluoropropylmethyl moieties. This general formula represents a siloxane component that can react with itself, with or without the presence of moisture and/or a catalyst in order to crosslink or polymerize into the silicone elastomer. If at least the R groups are alcohol moieties, the silicone elastomer can be formed by reaction with a suitable crosslinking component.

Exemplary silicone elastomers or rubbers are siloxane condensation reaction products from siloxane components such as poly(dimethyl siloxane), poly(ethylmethyl siloxane), poly(3,3,3-trifluoropropylmethyl siloxane), and copolymers of these types of siloxanes with poly(dimethyl siloxane). Polymeric siloxanes are generally known and are available commercially, for example, from The Dow Corning Company. Siloxanes are generally described in U.S. Pat. No. 3,434,869, the subject matter of which is incorporated by reference hereinto. These materials are hydrophobic and substantially nonpolar.

As is more fully described in my copending application entitled "Crack Prevention of Implanted Prostheses", the subject matter of which is incorporated by reference hereinto, these silicone rubber or silicone resin materials will be applied over the primer coating including the monomers according to the present invention while the silicone materials are dispersed or dissolved in a solvent that will not detrimentally affect the surface of the implanted device or the like that is being treated. Typically acceptable solvents in this regard include heptane, hexamethyldisiloxane, trichloroethane, polyhalogenated hydrocarbons, and the like. Certain of these, especially some polyhalogenated hydrocarbons, exhibit atmospheric boiling points that are below room temperature, which facilitate a flash evaporation of the solvent after application of the crack preventative composition over the primer coating.

Compositions containing the monomers according to this invention can be applied by any suitable means, such as immersion into a bath, spraying, brushing or the like. For example, when the monomers are used as primer coatings, the item to be treated is often able to be simply run through a bath containing the monomer. If the device has interstices or other types of undulations that are not easily contacted with a liquid by simple dipping procedures, it can be preferred to physically manipulate the device, such as squeezing same between rollers or presses, using increased quantities of diluents or solvent in the primer composition, repetitive coating steps, or the like. When the primer coating is used in conjunction with a crack preventative operation, the crack preventative composition can be similarly applied thereover.

EXAMPLE

Equal molar weights of methylene bisphenyl isocyanate and of 2-hydroxyethyl methacrylate were reacted together in a solvent in order to form 2-(methylene bisphenyl isocyanate) ethylmethacrylate. More particularly, a 60 percent solids solution of 2-hydroxyethyl methacrylate in dimethylacetamide was added very slowly to the methylene bisphenyl isocyanate, the slow addition being in order to prevent heat build-up created by the exothermic and rapid reaction between the two components. The thus formed 2-(methylene bisphenyl isocyanate) ethylmethacrylate and solvent composition was applied to a biocompatible polyurethane surface. The adhesion of this primer composition onto the polyurethane surface was observed, and the surface of the polyurethane developed a cloudy appearance which evidenced the coupling reaction. The primer composition was easily and safely handled as a non-volatile liquid at room temperature.

It will be understood that the embodiments of the present invention which have been described are illustrative of some of the applications of the principles of the present invention. Numerous modifications may be made by those skilled in the art without departing from the true spirit and scope of the invention.

I claim:

1. A treatment method for substantially preventing in vivo cracking of biocompatible surfaces of implanted devices for medical use, comprising:
   providing a shaped substrate having a biocompatible polymeric surface that is susceptible to cracking when subjected to implantation under in vivo conditions for substantial time periods;
   coating said biocompatible polymeric surface with a primer coating composition, said primer coating composition including a monomer having a an effective amount of general formula as follows:

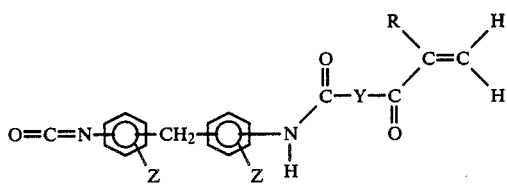

wherein R is H or $CH_3$, Y is NH or $X-R_1-X$, with X being O or NH and $R_1$ being a hydrocarbon chain having from about 1 to about 6 carbon atoms, and wherein Z is H or a hydrocarbon chain of from about 1 to about 3 carbon atoms; and
applying a crack preventative composition over the primer monomer coating coomposition.

2. The treatment method according to claim 1, wherein said monomer has a vapor pressure at room temperature such that the monomer is substantially non-volatile at room temperature.

3. The treatment method according to claim 1, wherein said monomer is a reaction product between an aromatic isocyanate and an acrylate having a terminal group with an active hydrogen moiety.

4. The treatment method according to claim 1, wherein, in said monomer, R is $CH_3$, Y is $X-R_1-X$ and $R_1$ has 2 carbon atoms, and Z is H.

5. The treatment method according to claim 1, wherein, in said monomer, R is $CH_3$, Y is $X-R_1-X$ and $R_1$ has 2 carbon atoms and both X moieties are O, and Z is H.

6. The treatment method according to claim 1, wherein said monomer is 2-(methylene bisphenyl isocyanate) ethylmethacrylate.

7. The treatment method according to claim 1, wherein said crack preventative composition includes a silicone rubber material having a surface tension that is less than a predetermined surface tension of the biocompatible polymeric surface.

8. The treatment method according to claim 1, wherein said crack preventative composition includes a silicone rubber material that is a siloxane which, prior to curing, has the formula:

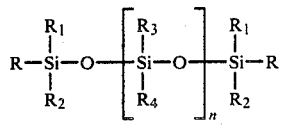

wherein each R group is an organic moiety selected from the group consisting of one or more ester moieties, acetoxy moieties and alcohol moieties, wherein each $R_3$ and $R_4$ group is an organic group selected from the class consisting of aliphatic groups and substituted aliphatic groups having from about 1 to about 12 carbon atoms, and aromatic groups and substituted aromatic groups having from about 6 to about 20 carbon atoms, and wherein each $R_1$ group and $R_2$ group is an organic component selected from the class consisting of R, $R_3$ and $R_4$.

9. A method for forming an implantable device for medical use, which device is treated to substantially prevent in vivo cracking thereof, the method comprising:
   providing a shaped substrate having a biocompatible polymeric surface that is susceptible to cracking when subjected to implantation under in vivo conditions for substantial time periods;
   coating said biocompatible polymeric surface with a primer coating composition, said primer coating composition including a monomer having a an effective amount of general formula as follows:

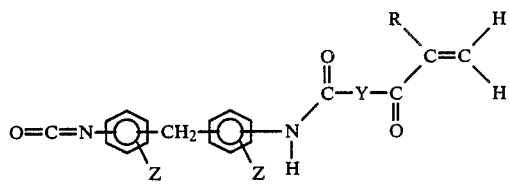

wherein R is H or $CH_3$, Y is NH or $X-R_1-X$, with X being O or NH and $R_1$ being a hydrocarbon chain having from about 1 to about 6 carbon atoms, and wherein Z is H or a hydrocarbon chain of from about 1 to about 3 carbon atoms; and
applying a crack preventative composition over the primer monomer coating composition.

10. The forming method according to claim 9, wherein, in said monomer, R is $CH_3$, Y is $X-R_1-X$ and $R_1$ has 2 carbon atoms, and Z is H.

11. The forming method according to claim 9, wherein said monomer is 2-(methylene bisphenyl isocyanate) ethylmethacrylate.

12. The forming method according to claim 9, wherein said crack preventative composition includes a silicone rubber material having a surface tension that is less than a predetermined surface tension of the biocompatible polymeric surface.

13. An implantable device for medical use under in vivo conditions, comprising:
   a shaped substrate having a biocompatible polymeric surface that is susceptible to cracking when subjected to implantation under in vivo conditions for substantial time periods;
   a primer coating onto said biocompatible polymeric surface, said primer coating including an effective amount of a monomer of the following general formula:

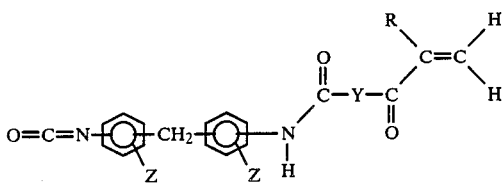

wherein R is H or $CH_3$, Y is NH or $X-R_1-X$, with X being O or NH and $R_1$ being a hydrocarbon chain having from about 1 to about 6 carbon atoms, and wherein Z is H or a hydrocarbon chain of from about 1 to about 3 carbon atoms; and a crack preventative component applied over said coated monomer and adsorbed to said substrate.

14. The implantable device according to claim 13, wherein said monomer is 2-(methylene bisphenyl isocyanate) ethylmethacrylate.

15. The implantable device according to claim 13, wherein said crack preventative composition includes a silicone rubber material having a surface tension that is less than a predetermined surface tension of the biocompatible polymeric surface.

16. The implantable device according to claim 13, wherein said biocompatible polymeric surface is a polymeric material selected from the group consisting of polyurethanes, poly(fluorosilicone urethane) copolymers, polyolefins, acrylate polymers, and other polymers having a surface tension greater than that of the crack preventative component.

* * * * *

UNITED STATES PATENT AND TRADEMARK OFFICE
CERTIFICATE OF CORRECTION

PATENT NO. : 4,769,030

DATED : September 6, 1988

INVENTOR(S) : Leonard Pinchuk

It is certified that error appears in the above-identified patent and that said Letters Patent is hereby corrected as shown below:

Col. 7, line 25, after "including" insert --an effective amount of--; lines 25-26, delete "an effective amount of" after "having a"; line 42, "coomposition" should read --composition--.

Col. 8, line 32, after "including" insert --an effective amount of--; lines 32-33, delete "an effective amount of" after "having a".

Signed and Sealed this

Twelfth Day of September, 1989

Attest:

DONALD J. QUIGG

Attesting Officer

Commissioner of Patents and Trademarks